US005508195A

United States Patent [19]

Christner et al.

[11] Patent Number: 5,508,195

[45] Date of Patent: Apr. 16, 1996

[54] METHOD FOR LIMING HIDES AND SKINS

[75] Inventors: Juergen Christner; Tilman Taeger, both of Seeheim-Jugenheim; Gertrud Wick, Darmstadt, all of Germany

[73] Assignee: Röhm GmbH, Darmstadt, Germany

[21] Appl. No.: 533,674

[22] Filed: Sep. 26, 1995

Related U.S. Application Data

[63] Continuation of Ser. No. 395,299, Feb. 27, 1995, abandoned, which is a continuation of Ser. No. 80,969, Jun. 22, 1993, abandoned.

[30] Foreign Application Priority Data

Jun. 25, 1992 [DE] Germany .......................... 42 20 838.6

[51] Int. Cl.$^{6}$ ................................ C12S 3/00; C12S 7/00; C12N 9/54; C14C 1/08

[52] U.S. Cl. .......................... 435/265; 435/262; 435/221; 8/94.18; 252/8.57; 252/188.2

[58] Field of Search .................................... 435/262, 265, 435/218, 221; 8/94.18; 252/8.57, 188.2

[56] References Cited

U.S. PATENT DOCUMENTS

| | | | |
|---|---|---|---|
| 3,939,040 | 2/1976 | Monsheimer et al. | 195/6 |
| 4,294,087 | 10/1981 | Monsheimer et al. | 69/21 |
| 4,960,428 | 10/1990 | Christner et al. | 8/94.18 |
| 5,089,414 | 2/1992 | Christner et al. | 435/265 |

FOREIGN PATENT DOCUMENTS

| | | |
|---|---|---|
| 0381952 | 12/1986 | Austria . |
| 0197918 | 10/1986 | European Pat. Off. . |
| 0306474 | 3/1989 | European Pat. Off. . |
| 0326059 | 8/1989 | European Pat. Off. . |
| 2047738 | 12/1980 | United Kingdom . |

OTHER PUBLICATIONS

"Microorganisms in Processing of Leather", Pfleiderer and Reiner, *Biotechnology*, vol. 6b, edited by Rehm and Reed, pp. 729–735 (1993).

*Primary Examiner*—Donald E. Czaja
*Assistant Examiner*—T. J. Reardon

[57] ABSTRACT

A method for liming hides and skins using a proteolytic enzyme in an aqueous-alkaline float is taught, wherein the liming float has a pH value from 10–14 and contains both thiourea dioxide and an alkaline protease having elastase activity.

5 Claims, No Drawings

METHOD FOR LIMING HIDES AND SKINS

This application is a continuation of application No. 08/395,299, filed Feb. 27, 1995 and now abandoned, which in turn is a continuation of application Ser. No. 08/080,969, filed Jun. 22, 1993 and now abandoned.

The present invention relates to a method for liming hides and skins wherein the aqueous liming float contains alkaline proteases together with thiourea dioxide.

In the course of the so-called beamhouse operations in the preparation of leather, an alkaline method step, liming, is used, which brings about the requirements for unhairing and effects the necessary opening of the hide structure (cf. Kirk-Othmer, *Encyclopedia of Chemical Technology,* 1st Edition, Volume 8, pp. 291–296; Ullmann's *Encyclopädie der technischen Chemie,* 3rd Edition, Volume 11, p. 560; 4th Edition, Volume 16, pp. 118–119; F. Stather, *Gerberei und Gerbereitechnologie,* Akademie-Verlag, Berlin 1967). In practise, so-called sharpened liming baths, predominantly a combination of calcium hydroxide and sodium sulfide, are used throughout. Details of performance of the method depend on whether the hair is to be destroyed or preserved. The dangers which arise because of dealing with inorganic sulfides in particular are sought to be avoided in different ways. Apart from the avoidance of conditions under which hydrogen sulfide can be liberated, there has been more recent interest in liming methods which are supported by enzymes. (Cf. E. Pfleiderer and R. Reiner in *Biotechnology,* H. J. Rehm & G. Reed, Editors, volume 6b, pp. 730–743, VCH, Weinheim 1988). In this case, mostly proteolytic enzymes [E.C.3.4], but also additionally lipases [E.C.3.1.1.3] and amylases [E.C.3.2.1] are used.

In order to reduce the content of potentially dangerous sulfide in waste water, the use of additional thio compounds, amines, and hydrotropic materials has been proposed. For example, unhairing can be carried out with thio compounds alone. However, this fact does not mean an end to the problem, since these materials also burden waste water and lead to annoying odors.

Enzymatic unhairing has always had only limited significance, principally for small animal skins and for obtaining wool. In contrast, the enzymatic unhairing of larger animal skins has not caught on, primarily because of an incomplete unhairing action, in part, and because of damage to the collagen grain-membrane or because of a too-strong decomposition of the skin materials. Even the joint use of alkaline proteases in liming together with small amounts of sulfides is not harmless. To be sure, the amount of sulfide can clearly be lowered by the use of enzymes and very good area yields are obtained with little grain draw, but nevertheless the leathers tend toward looseness of the grain, to a loose flank structure, and to a coarse, sometimes nubucked grain pattern.

Recently, the use of thiourea dioxide (THDO), or formamidine sulfinic acid was proposed as a replacement for sulfide (AT-PS 381,952; EP 197,918). This compound has a very high reduction potential toward cysteine so that a flawless unhairing can be carried out at dosages of 0.1–1 percent by weight together with calcium oxide or calcium carbonate. The compound is largely odorless and the degree of preservation of the hair is clearly better than with a pure sulfide liming. Further, the compound shows minimal waste water toxicity since there is good biological decomposition. Opposing these advantages are a relatively high price and the discovery that leathers prepared in this way do not have the optimum softness that products treated by conventional liming have. These reasons are probably why thiourea dioxide used alone has so far not succeeded. Thus, newer proposals involve using THDO together with hydrotropic materials and materials inhibiting swelling, e.g. amines, in order to get the desired opening of the hide structure with a corresponding amount of alkali (cf. EP 306,474). In part, THDO is used without further additives in after-liming because of its bleaching action, usually in amounts from 0.3 to 0.4 percent by weight of the pelts.

In view of the state of the art described, there is a technical need for a method that will combine the advantages of the traditional liming process with the positive effects of using thiourea dioxide. Particular attention was to be paid to the ecological compatibility of the method and the principles of activity involved.

It has now been found that the liming method according to the invention extensively complies with these demands.

The present invention thus pertains to a method for the liming of hides and skins in which the aqueous liming floats have a pH value in the range from 10–14, preferably 12–14, and contain thiourea dioxide and an alkaline protease AP having elastase activity. Preferably the floats contain 0.3 to 2 percent by weight, particularly 0.5–1 percent by weight, of thiourea dioxide together with an effective amount of one or more alkaline proteases AP. In the sense of the present invention, liming should be understood to include hair loosening, true liming, opening up of the hide, and, optionally, after-liming. It is important that in the method according to the invention, the presence of inorganic sulfides or of sulfide ions and of agents developing sulfide under the reaction conditions can be dispensed with. The combination of THDO and alkaline proteases according to the invention is thus outstandingly suitable for sulfide-free liming and/or after-liming as well as for liming/after-liming poor in sulfide.

For the characterization of elastases [E.C.3.4.21.11], their ability to hydrolyze elastin fibers of the aorta is relied on (W. Appel in *Methoden der enzymatischen Analyse,* H. U. Bergmeyer, Editor, 3rd Edition, Volume I, pp. 1081–1085, Verlag Chemie 1974; J. Mandel is *Methods of Enzymology,* S. P. Cholowick and N. O. Kaplan, Editors, Volume V, p. 665, Academic Press 1962).

Elastase preparations, even in crystalline form, must ab initio be considered to be non-uniform. Even the purest preparations still contain a portion of proteolytic, non-elastolytic activity. In structure and specific activity, the elastases seem to resemble trypsin and chymotrypsin.

Quantitative determinations are based on the decomposition (proteolytic as well as mucolytic) of elastin. Mostly, the decomposition of elastin loaded with dyes such as orcin (or congo red, dimethylamino naphthalene sulfonic acid) or fluorescein is involved.

The alkaline proteases AP having elastase activity are characterized by an activity optimum in the alkaline pH region, as a rule in the region pH 12 ±2.

Although other sources should not be excluded, microorganisms, particularly bacteria, and especially the bacilli at present represent the preferred starting materials.

Particularly to be mentioned are, e.g. *Flavobacterium elastolyticum, Chlortridium histolyticum, Staph. epidermis.* In the preparation of alkaline proteases from Bacillus types, in fact amounts of 30–60 percent by weight of alkaline proteases and 0.002–2 percent by weight of elastase are obtained, in addition to neutral proteinase and collagenase (cf. USSR-PS 802,909, Chem. Abstr. 94, 148340x).

Recently, alkaline elastases have been prepared as products of gene manipulation, e.g. by cloning of the alkaline elastase gene from *Bacillus alcalophilus* and expression in *Bacillus subtilis* [cf. JP-OS 90 76 586, Chem. Abstr. 115, 249561c; Y. Ch. Tsai et al., Biochim. Biophys. Acta 1986, 883 (3), 439–447; Appl. Environ. Microbiol. 1988, 54 (12)

3156–3161; Chem. Abstr. 110, 110535a; R. Kaneko et al, Japan. J. Bacteriol. 171 (9) 5232–5236 (1989)]. In the last-mentioned work, the isolation of an alkaline elastase YaB, which is produced extracellularly by the alkalophilic *Bacillus sp.YaB* and expression of the gene in *B.subtilis* is reported. Alkaline proteases with ca. 59 percent of elastase activity were also obtained from an Aspergillus (*A.versicolor* 837). (Cf. Chem. Abstr. 100, 66560x.) Other sources are Pseudomonas types, e.g. *P.aeruginosa* (cf. A. Lazdunski et al., Biochimie 1990, 72 (2–3) 147–156).

The determination of the elastase activity is, for the purposes of the present invention, undertaken by the method given in the experimental section. The units of elastase activity determined in the manner there reported are hereinafter designated as elastase units E.U.gly. For this purpose, the definition is that one elastase unit (E.U.gly) corresponds to the extinction of one μmol of glycine in the trinitrobenzene sulfonic acid determination; analysis conditions: substrate is elastin in a buffer at pH 8 and at 37° C. wherein the increase in extinction is evaluated per minute. According to the method of the invention, the activities of the active enzymes in the enzyme preparation AP are preferably in a defined relationship. This relationship is defined mathematically as follows: The protease activity of the alkaline protease [in Löhlein-Volhard Units (LVU)] divided by one thousand and multiplied by a factor, F, numerically give elastase activity in the units E.U.gly chosen for the purposes of the present invention (cf. experimental portion). According to the invention, the factor F is between 0.6 and 20, preferably 1 to 5.

The alkaline proteases [E.C.3.4.21] which can be used in the enzyme preparations AP used according to the invention are characterized in the usual way. [Cf. Kirk-Othmer, 3rd Edition, Volume 9, pp. 199–202, J. Wiley 1980; Ullmann's *Encyclopedia of Industrial Chemistry*, Volume A9, pp. 409–414; VCH 1987; L. Keay in Process Biochemistry, 17–21 (1971)]. These proteases, which mostly belong to the serine type, usually develop their activity optimum in a pH range from about 8–13. Bacterial proteases should be particularly mentioned, especially Bacillus strains, advantageously those which have original elastase activity. However, alkaline proteases of various origins can be combined with one another, in which case the elastase activity is to be introduced by a corresponding addition.

As such alkaline proteases, those obtained from Bacillus strains should be mentioned above all, especially from *B. subtilis,* but also *B. formus, B.licheniformis, B.alcalophilus, B.polymixa, B.mesentericus,* as well as those from Streptomyces strains such as *S.alcalophilus.*

The most favorable working temperature with alkaline bacterial proteases is in general at 40° C.–60° C. (which high temperature, however, must be clearly avoided in the present case) and more often at 20° C.–40° C. with fungal proteases.

As alkaline fungal proteases, those from Aspergillus strains are mentioned, such as *A.oryzae,* from Penicillium strains such as *P.cyanofulvum,* or *Paecilumyces persinicus.* The activity of the alkaline fungal proteases is predominantly in the pH region 8.0– 11.0.

The proteolytic activity of the alkaline proteases is conventionally determined according to the Anson Hemoglobin method [cf. M. L. Anson, J. Gen. Physiol. 22, 79 (1939)] or according to the Löhlein-Volhard method [modified according to TEGEWA, cf. Das Leder, 22, 121–126 (1971)].

According to this, one Löhlein-Volhard unit is that amount of enzyme which, in 20 ml of casein filtrate, will bring about an increase in hydrolysis product which corresponds to an equivalent of 5.75 ($10^{-3}$) ml of 0.1N NaOH. The protease activity to be used is in general between 1000 and 60,000 LVU per kg of hide, preferably between 2000 and 14,000 LVU per kg of hide.

Depending on activity—as a rule of thumb when using an alkaline bacterial protease (*Bacillus alcalophilus*) having 4000 LVU—amounts between 0.05 to 0.8 percent, preferably about 0.1 to 0.3 percent, of the protease are usually sufficient in the method of the invention, based on the weight of the hides and skins used.

According to the invention, 0.3–2 percent by weight, preferably 0.5–1 percent by weight of thiourea dioxide are used together with the proteolytic enzymes AP. The float length is as a rule 100 to 120 percent by weight of the hides and skins used.

Adjustment of the pH region of the float advantageously is accomplished using calcium hydroxide, however portions of sodium hydroxide and/or soda can also be used. For further improvement of the opening up of the hide structure, known agents such as organic amines, e.g. diethanolamine, and/or hydrotropic substances such as urea can be used as additives.

As usual, one starts with fresh or salted raw hides. In general a soak to remove dirt and a main soak are carried out as pretreatment (U.S. Pat. No. 4,344,762). The main soak is performed as is usual in the trade with the use of suitable proteases and/or of surfactants at a pH of 9–10 for 4–6 hours.

The float used in the main soak is conventionally drained and one proceeds with a new bath. In general, the enzymatic reaction is carried out in a temperature region from 20° C.–28° C., preferably at 26° C. The float, which is adjusted to an alkaline pH, especially in the region from 10–13, and which contains enzyme and the thiourea dioxide is left to act on the hides and skins in a conventional reaction vessel, for example a mixer, tanning vat, etc. with agitation, for a sufficient period of time until they are extensively free of hair, for which—as a rule of thumb—ca. 90 minutes can be mentioned.

Then the batch can be post-alkalinized with some alkali, for example 0.2 percent by weight of a 50 percent sodium hydroxide solution, preferably with agitation for about 30 minutes. This is followed by a longer treatment phase which is carried out for 18 hours, for example, suitably with short periods of agitation/longer periods of rest, in about the relationship: 1 minute agitation, 59 minutes rest. Then the float is drained. The hairs show less destruction than when conventional sulfide-lime liming is used. Advantageously there is an after-wash, for example two washings each with 200 percent portions of water at 25° C. for 15 minutes.

Further treatment can follow in the usual way, e.g. in the sequence bating/deliming/pickling/chrome tanning.

The method according to the invention permits the preparation of remarkably soft leathers, in which it is especially to be emphasized that despite the used of decomposing enzymes as a rule a completely intact grain pattern is present. Altogether the result is to be viewed as very surprising since the nubucking expected from the use of enzymes in liming as well as the expected loose grain in the flanks, occur so slightly.

By the use of enzymes in the scope of the method of the present invention, the required amount of thiourea dioxide can be clearly reduced. The combination of thiourea dioxide and alkaline protease in liming makes possible an ecologically extremely advantageous liming method which combines high leather quality with adequate safety in use. The ecological advantage is primarily in the good maintenance of the hair and the resultant reduced chemical oxygen demand in the waste water, as well as in the avoidance of any addition of sulfide.

The following examples serve for illustration of the invention.

EXAMPLES

Example 1–4

Raw goods:

1 metric ton (1000 kg) of salted or fresh cowhides, weight class 30–39 kg (dappled black).

Pretreatment:

Soak to remove dirt, main soak follows as conventional in the trade with the use of surfactants at pH 9–10 for 4–6 hours. The floats of the main soak are drained and in all examples further work takes place in a fresh bath.

All reported percentages are percentages by weight of the salted or green weight of the hides.

Example 1

Raw goods:
1 metric ton (1000 kg) of salted cowhides
Liming:
150.0% water, 26° C.
3.5% lime
0.8% thiourea dioxide
0.3% proteolytic enzyme, e.g. from *Bacillus alcalophilus,* pH activity optimum pH 10–13, 4000 LVU units, elastase value 6.4 (F=1.6)

Agitate for 90 minutes until the hides are extensively free of hair.
0.2% sodium hydroxide, 50%

Agitate for 30 minutes then treat for a further 18 hours (1 minute agitation, 59 minutes rest).

Drain the float (the hairs are less destroyed than in a conventional sulfide/lime liming).

Wash twice with 200% portions of water at 25° C. for 15 minutes.

Further conventional treatment with bating/deliming/pickling/chrome tanning.

Example 2

Raw goods:
metric ton (1000 kg) of fresh cowhides
Liming (hair-retaining):
100% water, 26° C.
1.0% lime, agitate for 90 minutes, pH 12–12.5
1.0% thiourea dioxide
0.3% proteolytic alkali-stable enzyme (e.g. from *Bacillus alcalophilus)* pH activity optimum pH 10–13, 4000 LVU
elastase value 6.0 (F=1.5)

Agitate for 90 minutes, pH 12–13, the hides are free of hair and well maintained structurally;

The hair can be separated by pumping out the float over a sieve.
+50% water, 26° C.
2.5% calcium hydroxide Agitate for 10 minutes
0.2% sodium hydroxide 50%

Treat for a further 15 hours (Automatically: agitate for 2 minutes, rest for 58 minutes): Drain the float. Wash twice each with 250% portions of water at 26° C. for 15 minutes.

Further treatment is as conventional in the trade.

Example 3

Raw goods:
1 metric ton (1000 kg) of salted cowhides
Low sulfide liming:
150.0% water, 26° C.
3.5% calcium hydroxide
0.4% sodium hydrogen sulfide, 72%

Agitate for 30 minutes.
0.4% thiourea dioxide
0.1% proteolytic, alkali-stable enzyme (e.g. from *Bacillus alcalophilus*), 4000 LVU, elastase value 6.8 (F=1.7).

Agitate for 60 minutes until the hides are free of hair.
+0.3% sodium hydroxide, 50%

Agitate for a further 18 hours (Automatically: 2 minutes agitation, 58 minutes rest).

Drain the float.

Wash twice with 150% portions of water, 25° C., 15 minutes.

Further treatment is as conventional in the trade.

Example 4

Conventional Sulfide/lime Liming and After-liming with a Combination of Active Materials According to the Invention for the Preparation, for example, of Especially Soft Furniture Leather with a High Color Uniformity Raw goods:
1 metric ton (1000 kg) of salted cowhides
Liming:
150% water, 26° C.
2.0% calcium hydroxide
0.9% sodium hydrogen sulfide Agitate for 20–30 minutes
1.0% calcium hydroxide, agitate for 20 minutes
0.4% sodium sulfide, 60%

Agitate for 30 minutes, then automatically: agitate for 2 minutes, rest for 58 minutes, for a total of 15 hours.

Drain the float, wash twice, flesh the hides and split to 1.8–2 mm.

After-liming:
150% water, 26° C.
1.0% calcium hydroxide
0.3% thiourea dioxide
0.1% proteolytic, alkali-stable enzyme (e.g. from *Bac. alcalophilus*), 4000 LVU, elastase value 9.2 (F=2.3).

Agitate for 20 minutes, then, for a further 6 hours: agitate for 2 minutes, rest for 58 minutes.

Drain the float, wash, and treat further as conventional in the trade.

DETERMINATION OF THE ELASTASE ACTIVITY OF THE ENZYMES USED ACCORDING TO THE INVENTION

Principle

A suspension of elastin at pH=8 is incubated at 37° C. for 2 hours with enzyme, the incubation then being interrupted by separating the substrate by filtration. The solution is then colored with trinitrobenzene sulfonic acid (TNBA) and its optical density at 420 nanometers is measured.

Definition 1 elastase Unit is that amount of enzyme which, per minute in an elastin suspension under the prescribed standard conditions of the test, develops a coloration with TNBA equivalent to 1 μmol of glycine.

Reagents:

Elastin (Sigma Lot 71 F-8020; No. E-1625)

Boric acid (p.a.=per analysis)

Trinitrobenzene sulfonic acid (TNBA)

Glycine

Apparatus:

Shaking thermostat: 37° C.

Water bath: 50° C.

Solutions:

1. 0.1M borate buffer, pH=8.0

A solution of 6.2 g of boric acid p.a is adjusted with 1N NaOH to pH=8.0 and brought to 1 liter with distilled water.

2. TNBA Reagent

Add about 800 ml of distilled water and 6.2 g of boric acid p.a. and bring to pH=8.0 with 1N NaOH. 240 g of TNBA are added to this, the pH is optionally adjusted again, and the mixture is brought to 1 liter with distilled water. The TNBA reagent is suitably stored in a brown bottle and is replaced fresh daily.

Reaction:

Main Value 250 mg of elastin are weighed into a 50 ml narrow mouth Erlenmeyer flask having a ground glass stopper and are combined with 10 ml of 0.1M borate buffer. The flask is earlier pre-heated in the shaking thermostat for 10 minutes. After the addition of 1 ml of enzyme solution, the contents of the flask are mixed well and the flask is returned to the shaking thermostat at 37° C.

The reaction is stopped after exactly 2 hours by filtering the reaction mixture through a folded filter. Coloration of the fragments using the TNBA Method follows directly.

TNBA Reaction:

100 μl of the sample are added to 8 ml of the TNBA reagent and the reaction time is stored by 25 minutes in a water bath at 50° C. After exactly 25 minutes, the tube is put into ice water and the extinction at 420 nm is measured directly afterward.

Blind value:

In this case the enzyme solution is first added after the expiration of the second hour of the reaction time. Further treatments follows as for the main value, namely it begins with the stopping of the reaction.

Creation of a Calibration Curve with Glycine:

The coloration of glycine with TNBA is measured and μmol of glycine are plotted against values of optical density.

Procedure:

3.75 g of glycine are dissolved in 100 ml of distilled water, from which 0.25 ml are removed and diluted to 500 ml. 100 μl of this sample were taken and colored according to the TNBA method. Measurement of optical density at 420 nm followed. Other samples were prepared in corresponding fashion. An example for the construction of a calibration curve is given in the following Table.

| Amount glycine weighed (in g) | Glycine concentration (μmol/ml) | Optical Density at 420nm |
|---|---|---|
| 3.75/100–0.25/500 | 0.25 | 0.30 |
| 3.75/100–0.25/250 | 0.5 | 0.058 |
| 3.75/100–0.50/250 | 1.0 | 0.110 |
| 3.75/100–1.00/250 | 2.0 | 0.232 |
| 3.75/100–1.00/200 | 2.5 | 0.313 |
| 3.75/100–1.50/200 | 3.75 | 0.496 |

Blind value:

The extinction value measured on a mixture of TNBA reagent+ 100 μl distilled water is subtracted from all the glycine values.

Calculation of Enzyme Activity:

The difference in optical density values measured in the activity determination (main value less blind value) is converted from the calibration curve into μmol glycine, from which the elastase units can be determined by the following formulas:

$$E.U.\text{gly} = \text{elastase units/mg} = \frac{(\mu\text{mol gly, read from the calibration curve}) \times 11 \times 100}{120 \text{ min} \times \text{concentration } (C) \text{ of enzyme (in mg)}}$$

$$\frac{(\mu\text{mol gly, read from the calibration curve}) \times 91.7}{\text{concentration } (C) \text{ of enzyme (in mg)}}$$

What is claimed is:

1. A method for liming hides and skins which comprises treating said hides and skins in an aqueous alkaline float suitable for liming and having a pH value from 10–14 until hair has been removed from them, said float comprising A) thiourea dioxide in an amount from 0.3–2 percent by weight of the hides and skins treated;

B) alkaline protease activity, LVU, in a range equivalent to that of a protease having an activity of 4000 LVU present in an amount which is 0.05–0.8 percent by weight of the hides and skins treated; and C) alkaline elastase activity, E.U.gly, the value of which is related to the activity of the protease by the relationship $$E.U.\text{gly (alkaline elastase)} = F \times \frac{LVU \text{ (alkaline protease)}}{1000}$$

where F has a value from 0.6–20.

2. The method as in claim 1 wherein the liming float is free of any sulfide addition.

3. The method as in claim 1 wherein the alkaline protease is a bacterial protease.

4. The method as in claim 3 wherein the alkaline bacterial protease is obtained from *Bacillus alcalophilus.*

5. The method as in claim 4 wherein F has a value from 1–5.

* * * * *